US011969547B2

(12) United States Patent
Boyes et al.

(10) Patent No.: US 11,969,547 B2
(45) Date of Patent: Apr. 30, 2024

(54) MULTI-DOSE MEDICAMENT DELIVERY DEVICE

(71) Applicant: Indosys Limited, Cheshire (GB)

(72) Inventors: Robert Nichol Boyes, Hertfordshire (GB); Philip Wilson Braithwaite, Cheltenham (GB)

(73) Assignee: Indosys Limited, Cheshire (GB)

( * ) Notice: Subject to any disclaimer, the term of this patent is extended or adjusted under 35 U.S.C. 154(b) by 727 days.

(21) Appl. No.: 16/638,534

(22) PCT Filed: Aug. 30, 2018

(86) PCT No.: PCT/GB2018/052453
§ 371 (c)(1),
(2) Date: Feb. 12, 2020

(87) PCT Pub. No.: WO2019/043390
PCT Pub. Date: Mar. 7, 2019

(65) Prior Publication Data

US 2020/0179626 A1 Jun. 11, 2020

(30) Foreign Application Priority Data

Aug. 30, 2017 (GB) ...................................... 1713899

(51) Int. Cl.
*A61M 15/08* (2006.01)
*A61M 15/00* (2006.01)

(52) U.S. Cl.
CPC .......... *A61M 15/08* (2013.01); *A61M 15/003* (2014.02); *A61M 15/0045* (2013.01); *A61M 2202/064* (2013.01); *A61M 2205/073* (2013.01)

(58) Field of Classification Search
CPC ................ A61M 15/08; A61M 15/003; A61M 15/0045; A61M 2202/064; A61M 2205/073; A61M 2205/071; A61M 15/0028
See application file for complete search history.

(56) References Cited

U.S. PATENT DOCUMENTS

| | | | |
|---|---|---|---|
| 7,270,127 | B2 | 9/2007 | Lockhart et al. |
| 8,201,555 | B2 | 6/2012 | Chawla |
| 2007/0051362 | A1 | 3/2007 | Sullivan et al. |

(Continued)

FOREIGN PATENT DOCUMENTS

| | | | |
|---|---|---|---|
| JP | 4986192 | B2 * | 7/2012 |
| WO | 2014012069 | A2 | 1/2014 |

OTHER PUBLICATIONS

Machine Translation of JP4986192B2, accessed Sep. 30, 2022 (Year: 2022).*

(Continued)

*Primary Examiner* — Elliot S Ruddie
(74) *Attorney, Agent, or Firm* — K&L GATES LLP

(57) ABSTRACT

There is described a multi-unit dose dry powder medicament delivery device comprising: a first element comprising a single use nozzle located in a body which is at least partially lined with an inner member, said inner sleeve comprising an airway and a cartridge seat; and a second element adapted to be releasably attached to the first element, said second element comprising an actuator provided with an air source and a valve.

13 Claims, 17 Drawing Sheets

(56) References Cited

U.S. PATENT DOCUMENTS

| | | | | |
|---|---|---|---|---|
| 2009/0241949 | A1* | 10/2009 | Smutney | A61M 15/0028 128/203.15 |
| 2014/0014106 | A1* | 1/2014 | Smutney | A61M 15/00 128/203.15 |
| 2014/0364837 | A1* | 12/2014 | Boyes | A61M 15/0028 604/514 |

OTHER PUBLICATIONS

PCT International Search Report and PCT Written Opinion for PCT International Patent Application No. PCT/GB2018/052453; dated Nov. 30, 2018; (12 pages).

* cited by examiner

MULTI-DOSE MEDICAMENT DELIVERY DEVICE

FIELD OF THE INVENTION

The present invention relates to novel multi-dose dry powder medicament delivery device, uses thereof and methods of manufacture.

More particularly, the invention relates to novel multi-dose/multi-use dry powder medicament delivery device which is suitable for use as, for example, a nasal medicament delivery device for the delivery of medicaments, e.g. for the treatment of a respiratory disorder and especially for the delivering of a vaccine or a hormone, such as, glucagon, in dry powder form.

The medicament delivery device is also suitable for use for the delivery of a medicament in, e.g. in powder form, into an infusion bag, the medicament then being delivered to the patient as a fluid infusion, for example, as an 'IV drip'.

BACKGROUND TO THE INVENTION

In recent years drug formulations have been developed in dry powder form, e.g. for delivery by inhalation, or by admixing in a solution for delivery by intravenous infusion. Such dry powder formulations include existing compounds reformulated into dry powder form and newly developed compounds, used in the treatment of many conditions and diseases.

Drug formulations in the form of inhaled dry powders offer advantages over other forms such as liquids and tablets, particularly when considering storage and stability.

Oral or nasal delivery of a medicament using a dry powder medicament delivery device is a particularly attractive method of drug administration as such devices can be relatively easy for a patient to use. As well as delivering medicament to treat local diseases of the airway and other respiratory disorders, dry powder medicament delivery devices have more recently also be used to deliver drugs to the bloodstream via the lungs or nasal passages, thereby avoiding, for example, the need for injections.

One advantage of delivering a drug in a dry powder form is that very low dosages of the medicament may be used. However, in many situations the disadvantage of using dry powder formulations lies in the complication of actual delivery to the patient's area of treatment and/or the metering of very low dosages of medicament. The principle problem lies in the accurate metering and containment of a unit of dose and subsequent appropriately controlled release or dispensing of the unit dose. This is a significant impediment for the pharmaceutical industry in developing the potential of dry powder formulations to end products.

Dry powder delivery devices are most commonly known in the form of dry powder inhalers, these range from metered dose devices such as Clickhaler® where the dry powder medicament is stored in a reservoir and metered by operation of the device; to unit dose devices where the medicament is stored in individual unit doses in capsules (e.g. Spinhaler®) or foil blisters (e.g. Diskhaler®). These devices are generally cumbersome and complex in construction and, although suitable for their intended use for delivering medicament to the lung, their adaption for delivery to other areas of treatment, such as the nasal passage and/or nasal cavity, is generally unsatisfactory.

The present invention seeks to provide a dry powder medicament delivery device that overcomes or substantially alleviates the problems with conventional inhalation devices and/or infusion devices. In particular, the invention seeks to provide a device having a significantly simpler construction than known devices. The dry powder medicament delivery device of the present invention is also easier to manufacture, assemble and operate, as well as being cheaper to manufacture. The present invention also seeks to provide a device that has the ability to re-use the air source and valve, and accommodate a single use nozzle and drug cartridge, thereby reducing cost and eliminating waste.

International Patent application No. WO 2013/088112 describes a single dose disposable dry powder medicament delivery device comprising a medicament container containing a unit dose of dry powder medicament, a medicament dispensing assembly and an air source. However, in the development of the aforementioned single dose disposable dry powder medicament delivery device the requirement for further improvements emerged.

Furthermore, recently dry powder intranasal vaccines have been developed. There are a number of advantages to intranasal delivery of drugs, in particular in dry powder form. Intranasal drug delivery offers rapid uptake into the blood stream by absorption through the nasal mucosa, the potential to reduce or eliminate cold chain management of vaccines during storage and transportation, and the elimination of needles and the potential for needle stick injuries.

Intranasal vaccination represents an attractive non-invasive alternative to needle-based injection and provides superior protection at mucosal surfaces. However, new formulations and delivery devices are needed to improve efficacy and reduce the refrigerated storage and distribution requirements associated with standard liquid vaccines.

Vaccines formulated as liquids can be subject to chemical degradation, e.g., aggregation, denaturation, hydrolysis, and oxidation that can result in their inactivation. Liquid vaccine formulations can also be sensitive to temperature: high temperatures can increase inactivation, and freezing temperatures can result in ice that can damage antigen in the vaccine. Thus, to prevent inactivation, liquid vaccines often must be stored at a temperature range of from 2-8° C.

The mode of administration of a vaccine can play a role in its efficacy. One mode of administration, non-parental administration (e.g., nasal), can induce and promote mucosal and systemic immune responses. In addition, nasal mucosa can help bind a virus or other pathogen at the mucosal surface, preventing access of the pathogen to deeper tissues and/or decreasing the likelihood of full-blown infection.

SUMMARY OF THE INVENTION

As described herein, the principal improvement over the device described in International Patent application No. WO 2013/088112 was to develop a device that offered the ability to reuse the air source and valve; and accommodate a single use nozzle and drug cartridge, thereby reducing cost and eliminating waste.

Therefore, according to a first aspect of the invention there is provided a multi-unit dose dry powder medicament delivery device comprising:

- a first element comprising a single use nozzle located in a body which is at least partially lined with an inner sleeve, said inner sleeve comprising an airway and a cartridge seat; and
- a second element adapted to be releasably attached to the first element, said second element comprising an actuator provided with an air source and a valve.

The multi-unit dose dry powder medicament delivery device of the invention will generally be used in conjunction with a cartridge comprising a dry powder medicament.

The medicament cartridge may comprise a unit dose of drug or medicament. The medicament cartridge comprises an elongate member provided with an inset cavity which acts as a medicament reservoir. The medicament cartridge will desirably be provided with a closure sleeve, said closure sleeve being slidably mounted around the inset cavity.

An important aspect of the airway of the inner sleeve is that it comprises at least one baffle element such that, in use, the medicament powder is caused to flow in a non-linear pathway before being expelled from the nozzle of the delivery device. Indeed, the airway of this aspect of the invention is such that the medicament powder is caused to substantially flow via at least two angular turns, e.g. right angled turns, i.e. a first right angle turn followed by a second right angle turn as it is expelled from the delivery device. Preferably, two angular turns are present. This provides a significant advantage in efficiently deagglomerating the powder whilst not impeding the efficient clearing of the entire dose from the drug cavity of the cartridge with sufficient velocity for the powder to reach its intended target, for example, the nasal cavity.

The elongate member of the medicament cartridge and slidable outer sleeve together provide a simple secure storage compartment for the powdered medicament which, when activated, also provide an effective means of powder deagglomeration as herein described.

However, although a cartridge comprising an elongate member and slidable outer sleeve is to be preferred, it will be understood by the person skilled in the art that a variety of known unit dose medicament containers may suitably be used in the dry powder medicament delivery device. Thus, for example, the unit dose dry powder formulation may comprise a pre-packaged capsule or blister, which each contains an individual dose, usually in the form of dose of the powder, which has been accurately and consistently measured. The use of a pre-packaged capsule or blister may be suitable if combined with a shuttle valve as herein described.

As herein described a medicament dispensing assembly generally comprises a body and a nozzle. More particularly, the medicament dispensing assembly comprises a body, a nozzle and an airway, the airway being provided with an inlet and an outlet, e.g. an air inlet and an air/medicament outlet. For an intranasal delivery device, the nozzle is desirably sized and shaped to be suitable for placing inside a patient's nostril. Although it will be understood by the person skilled in the art that the medicament dispensing assembly may also be designed so as to be suitable for oral delivery, such as an inhaler for delivery to the lungs (respiratory tract).

The releasable attachment of the first element to the second element may comprise a snap-fit, screw fit, bayonet fit and the like. In a preferred aspect of the invention the releasable attachment comprises a screw fit.

In a further aspect of the invention the inner sleeve may be provided with a shuttle valve. A shuttle valve will be dimensioned such that in the closed position it blocks the airway only until the device is primed by a user. The shuttle valve may be provided with a pair of orifices which, when the delivery device is primed, align with the airway of the device. The use of a shuttle valve is advantageous in that it can reduce the potential for medicament powder spillage if the device is inverted or shaken.

In use, the delivery device comprising a shuttle valve goes through three states once the nozzle has been engaged:

(i) nozzle engaged;

(ii) nozzle screwed in and primed; and (iii) the device is actuated/fired.

The use of a shuttle valve acts to block the airways in step (i); in step (ii) the shuttle valve is released from its detent, but the airways remain closed by the valve; when the device is actuated in step (iii) the shuttle valve moves to an "open" position and the airways are unblocked.

The actuator in the second element may comprise a spigot element which, when inserted into the first element, pushes the medicament container into position for delivery of the medicament. Preferably the spigot element is provided with at least one aperture to enable air to pass from the air source and valve through the spigot.

The air source may comprise a delivery pump e.g. it may comprise a syringe. Such a syringe may, for example, comprise a conventionally known propriety syringe, e.g. a disposable syringe, or may comprise a conventionally known means for ejecting an air stream, for example, an insufflator or other such apparatus suitable for blowing air or gas upon activation, such as a cylinder and piston, bellows, a squeezable bulb or a compressed air or gas source such as a compressed air canister or from a compressed air system fitted with suitable volume and pressure control apparatus. In a preferred aspect of the invention the air source comprises bellows.

The use of a valve in the second element of the delivery device of the invention is advantageous in that it allows the volume, pressure and velocity of air that passes through the device to be controlled. The valve used in the delivery device of the present invention is a burst valve. In a preferred aspect of the invention a particular burst valve is used which is novel per se.

Thus, according a further aspect of the invention there is also provided a novel burst valve, suitable for use with a dry powder delivery device, said burst valve comprising a moulded flexible polymer disc provided with a circumferential flange to provide a sealing ring. Substantially in the centre of the disc there is provided a pyramid structure which forms a closure. The pyramid structure may comprise any number of sides. Preferably, the pyramid structure may comprise 3 to 8 sides, preferably 3 to 5 sides and especially 3 or 4 sides. A sided pyramid is most preferred. In a particular aspect of the invention the centre of disc is provided with a frustum of a pyramid as herein described, e.g. a frustum of a pyramid.

The pyramid structure is provided with at least one slit cut from the pyramid. Preferably, the at least one slit is cut along a diagonal of the pyramid. For the avoidance of doubt, the slit is cut as opposed to formed, because it should be understood that the slit remains closed in its dormant state. The pyramid structure may be provided with more than on slit, e.g. two slits, i.e. a slit along each of two diagonals, but a single slit is preferred.

The moulded flexible polymer may comprise a silicon polymer, but a preferred polymer is a Thermoplastic Elastomer (TPE) which is flexible, resilient non-porous and elastomeric.

The use of a thermoplastic elastomer is advantageous due to the ability of a thermoplastic elastomer to stretch to moderate elongations and return to its near original shape creating a longer life and better physical range than other materials. Thermoplastic elastomers generally have excellent flexural fatigue resistance, good tear & abrasion resistance, high impact strength, resistance to chemicals and are recyclable.

Exemplary commercially available TPEs include, but shall not be limited to, Pebax®, Arnitel®, Riteflex®, Enflex®, Ensoft®, Sconablend® and Ravathane®.

The use of a burst valve may be advantageous in that by positioning a dispersible dry powder material, e.g. a medicament material, downstream of a burst valve; causing the valve to open will produce a rapid depletion of the air pressure up-stream of the valve through the air-path in the device that disperses and/or deagglomerates the material. A burst valve may be fitted between the air source and the (intranasal) delivery device so that when the valve opens at a certain predetermined air pressure the velocity of the air rushing through the device will clear it very effectively.

According to the invention there is provided a method of producing an aerosol of a dry powder which comprises positioning a dispersible dry powder material, e.g. a medicament material, downstream of a burst valve member; wherein causing the valve member to flex and open will produce a rapid depletion of the air pressure up-stream of the valve or diaphragm through the air-path in the device that disperses and/or deagglomerates the material.

In one embodiment, the dry powder medicament delivery device comprises a medicament delivery device, e.g. a nasal inhaler. However, in a further embodiment drug carrier is utilised in a device to facilitate application of the drug in dry powder form via an air flow to the vagina or rectum, such a device may be fitted with a means to dilate the vagina or rectum.

The dry powder medicament delivery device according to this aspect of the invention may be suitable for delivery of a variety of medicaments and may be suitable for use in the treatment of a variety of disorders.

Thus, for example, for use as an inhaler, e.g. an inhaler for oral drug delivery, or a nasal dry powder medicament delivery device, e.g. a nasal inhaler, a variety of medicaments may be administered. Such medicaments are generally suitable for the treatment of asthma, COPD and respiratory infections. Such medicaments include, but are not limited to 2-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratropium bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide, flunisolide and ciclesonide, and isomers and/or salts or derivatives thereof.

Specific combinations of medicaments which may be mentioned include combinations of steroids, such as, beclomethasone dipropionate and formoterol; beclomethasone dipropionate and salmeterol; fluticasone and formoterol; fluticasone and salmeterol; budesonide and formoterol; budesonide and salmeterol; flunisolide and formoterol; and flunisolide and salmeterol. It is also within the scope of this invention to include combinations of one or more of the aforementioned steroids with one or more of the aforementioned β2-agonists.

However, there is increasing interest in the pulmonary delivery or intravenous delivery of medicaments due, inter alia, to the rapid onset of their efficacious effect. Thus, further medicaments which may be mentioned include systemically active materials, such as, proteinaceous compounds and/or macromolecules, for example, hormones and mediators, such as insulin, glucagon, human growth hormone, leuprolide and alpha interferon, growth factors, anticoagulants, immunomodulators, cytokines and nucleic acids. Other medicaments which may be mentioned are those for the treatment of neurological disorders, such as Parkinsonism, such as, levodopa, carbidopa, benserazide, selegiline, tolcapone, entacapone, bromocriptine, lysuride, pergolide, ropinirole and cabergoline; or migraine, such as divalroex sodium, ergotamine, methysergide, metoprolol, propranolol, zolmitriptan, vigabatrine, clonidine, ganaxolone, lysine acetylsalicylate, sumatriptan, naratriptan, timolol, almotriptan, cyproheptadine, rizatriptan, timotol, dotarizine, dihydroergotamine, metysergide, pizotifen, eletriptan, prochlorperazine, nadolol and frovatriptan. In addition, medicaments for the treatment of sexual dysfunction may be mentioned. Such disorders include erectile dysfunction where treatments include administration of phosphodiesterase type-5 (PDTE5) inhibitors, such as tadalafil, vardenafil and sildenafil; and premature ejaculation, where treatments include administration of selective serotonin reuptake inhibitors, such as dapoxetine.

However, one particular aspect of the present invention provides the dry powder medicament delivery device as herein described as a nasal dry powder medicament delivery device. A nasal dry powder medicament delivery device according to this aspect of the invention may be suitable for the delivery of any of the medicaments herein described.

An important use of the delivery device of the present invention is for the delivery of an emergency therapy. The intranasal or intravenous route of drug delivery can afford rapid absorption of drugs into the blood circulation. For example, the intranasal route can also offer a less invasive route of drug administration compared with some other routes such intravenous or intramuscular injection. Such rapid and effective drug delivery can be useful in the treatment of crisis situations such as pain, convulsions, serious hypoglycaemic reaction, etc.

The delivery device of the present invention is found to be especially advantageous in the delivery of a medicament in an emergency situation, for example, where the patient is unconscious. The nasal delivery device of the invention is especially useful in a situation where medical staff are not available. One specific such therapy is the intranasal administration of a therapeutically effective amount of glucagon to a diabetic who is experiencing a serious hypoglycaemic reaction. Glucagon is a hormone that causes the liver to release glucose into the blood and is used to quickly increase blood sugar levels in diabetics with hypoglycaemia (low blood sugar). Glucagon is usually provided in powder form and given as an injection either into a vein, an arm or leg muscle or under the skin as directed, usually to an unconscious patient. The glucagon powder must first be dissolved in a diluting fluid and must be used immediately after it has been mixed.

Therefore, according to a particular aspect of the present invention there is provided a method of delivering glucagon to a patient which comprises the use of a medicament delivery device as herein described, especially the use of a dry powder nasal dry powder medicament delivery device.

A further category of patients for whom intravenous or intramuscular injection may be problematical is infants and young children, therefore the use of the delivery device of the present invention as an intranasal, oral or rectal drug delivery device may be beneficial.

In addition, when used as an inhaler, e.g. an oral inhaler and especially a nasal dry powder medicament delivery device, the medicament delivery device as herein described may suitably be used for the delivery of one or more dry powder vaccines.

Dry powder vaccine compositions for intranasal delivery are described in International Patent application No. WO 2011/129120. Therefore, a dry powder vaccine for use in association with a medicament delivery device, such as a nasal dry powder medicament delivery device, of the present invention, can be useful for the prevention and/or treatment of infection by any virus.

However, it will be understood by the person skilled in the art that the dry powder medicaments mentioned herein can be delivered using the delivery device of the present invention, to deliver a dry powdered medicament to, for example, an intra-venous infusion bag.

In a further embodiment a medicament carrier may be utilised in a device to facilitate application of the medicament in dry powder form, by entraining the powder in a gel for administration to a body orifice.

In a yet further embodiment a medicament carrier may be utilised in a device to facilitate dermal or transdermal application of the drug in dry powder form, via a gel applicator.

It will be appreciated that the above descriptions can apply to the treatment of animals as well as humans.

The invention further provides a method of delivering a medicament, e.g. a dry powder medicament, to a patient which comprises the use of a dry powder medicament delivery device as herein described.

Fluid may be prevented from leaking from the device by a seal which has a circumferential seal feature to seal against a seal housing within the main body and a face seal feature to seal against the face of the medicament carrier.

The invention further provides a method of treatment of a patient with a disorder which comprises the administration of a medicament using a medicament delivery device as herein described.

The method of treatment according to this aspect of the invention may comprise the administration of any one or more of the therapeutically active agents described herein. However, there is especially provided a method of delivering a vaccine, e.g. a dry powder vaccine to a patient.

More especially, the invention provides a method of treating a patient which comprises the administration of a therapeutically effective amount of glucagon to a diabetic experiencing a hypoglycaemic reaction.

Desirably the inner sleeve comprises a suitable first plastics material and the medicament cartridge, comprising an elongate member provided with an inset cavity, comprises an alternative second plastics material. The preferred device, i.e. comprising first and second plastics materials may be manufactured by a variety of methods, including a method known as two shot moulding or injection moulding.

The term 'suitable' plastics material as herein described is intended to mean, for example, first and second plastics material that do not to bond to each other. The lack of bonding between the first and second plastics material allows the sleeve to slide over the elongate member.

Thus, according to a further aspect of the invention there is provided a method of two shot moulding a medicament container comprising an elongate member comprising a suitable first plastics material and the slidable sleeve comprises an alternative second plastics material.

The unit dose medicament container as herein described is advantageous in that, inter alia, it is easy and economic to manufacture and can be easily filled either on an individual basis or in a fast moving production line. One method of filling is described in the specific embodiments herein.

According to a further aspect of the invention there is provided a dry powder medicament delivery device kit comprising:

- a first element comprising a single use nozzle, said nozzle being located on a body which is at least partially lined with an inner sleeve, said inner sleeve comprising an airway and a cartridge seat;
- a second element adapted to be releasably attached to the first element, said second element comprising an actuator provided with an air source and a valve; and at least one cartridge comprising a dry powder medicament.

The kit according to this aspect of the invention which includes a plurality of medicament cartridges.

The invention will now be described by way of example only and with reference to the accompanying drawings in which FIG. 1 is a cross-sectional view of a nozzle with an inner sleeve and cartridge assembly;

Figure 4A:
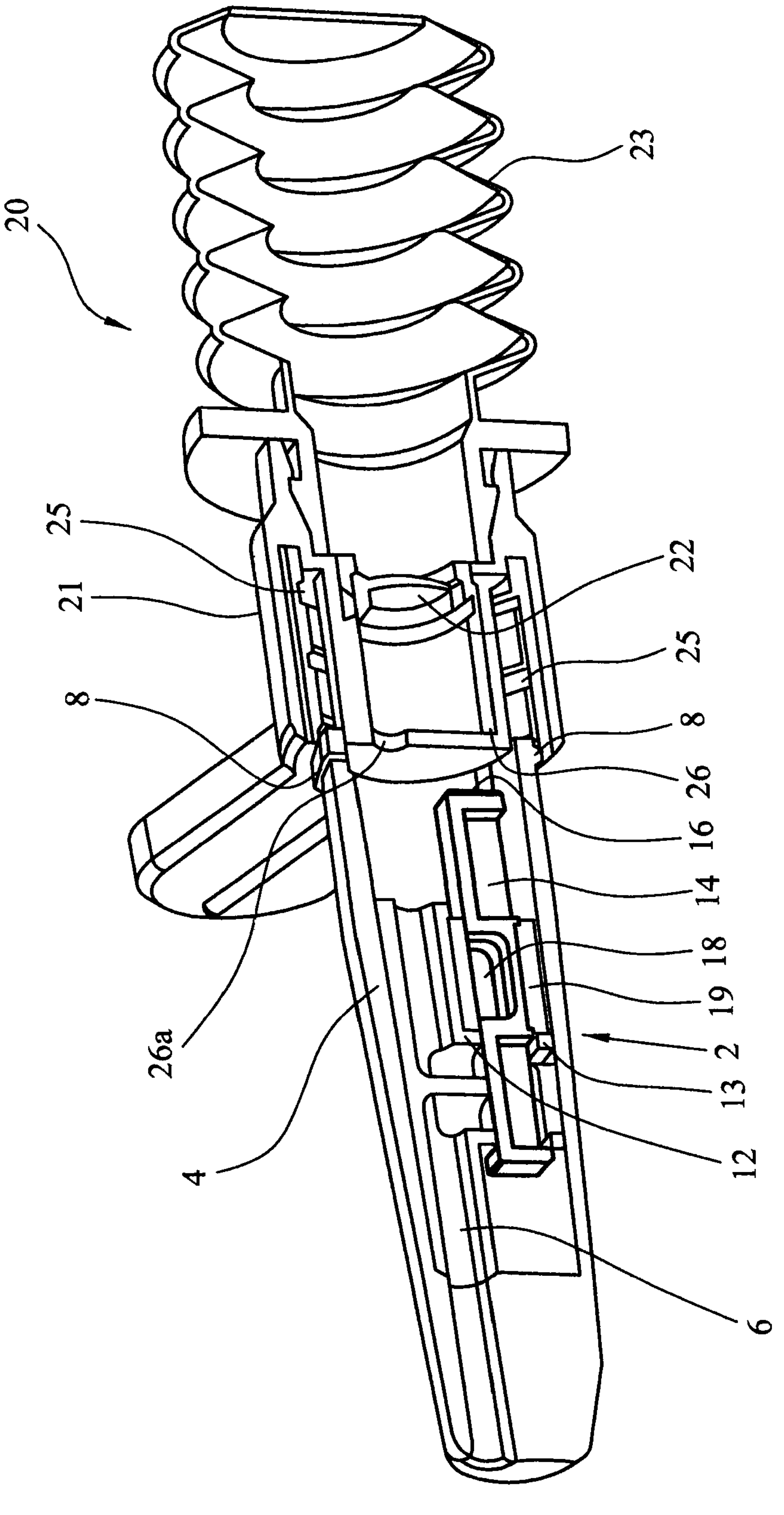
Figure 4B:
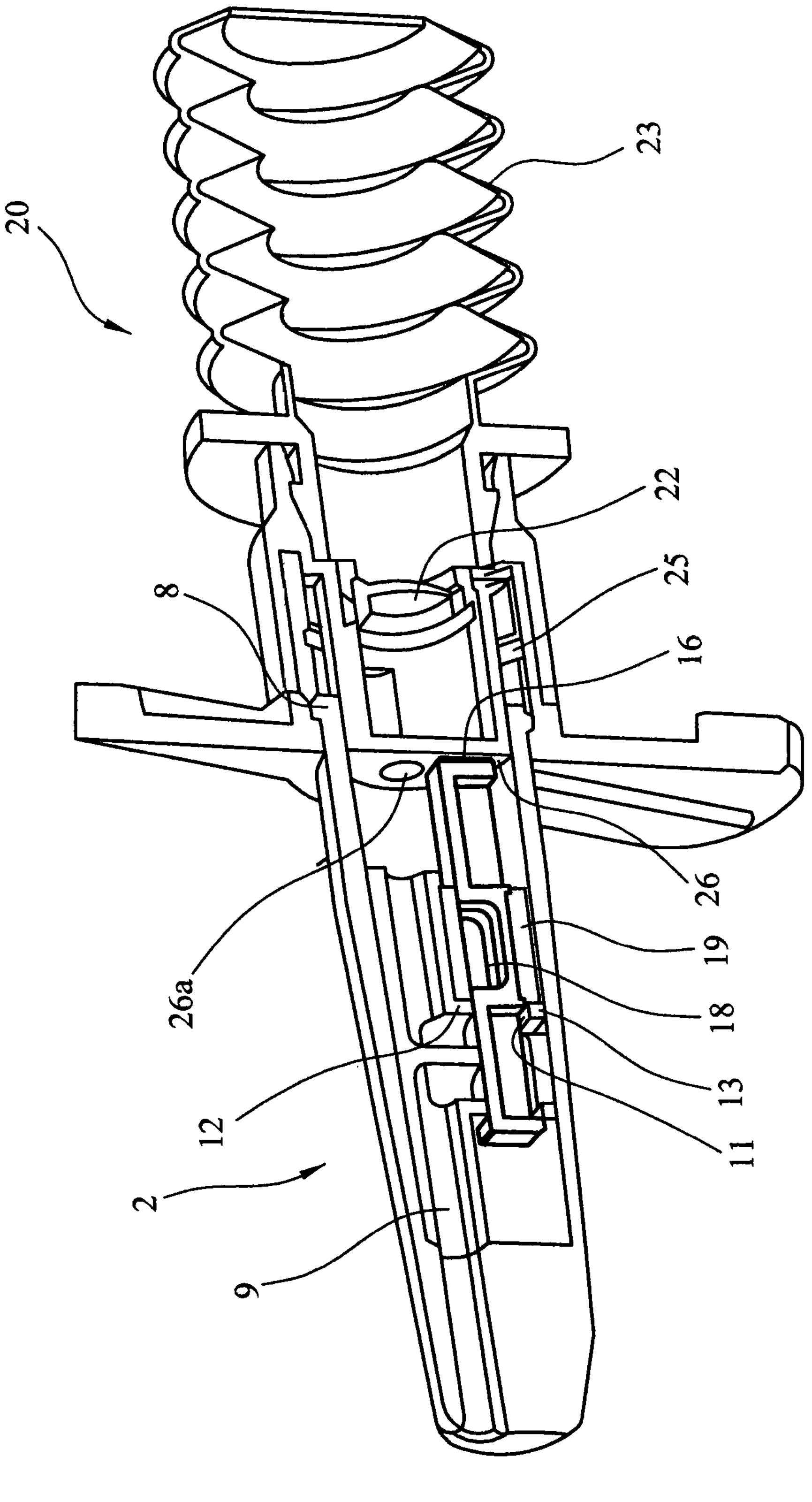
Figure 4C:
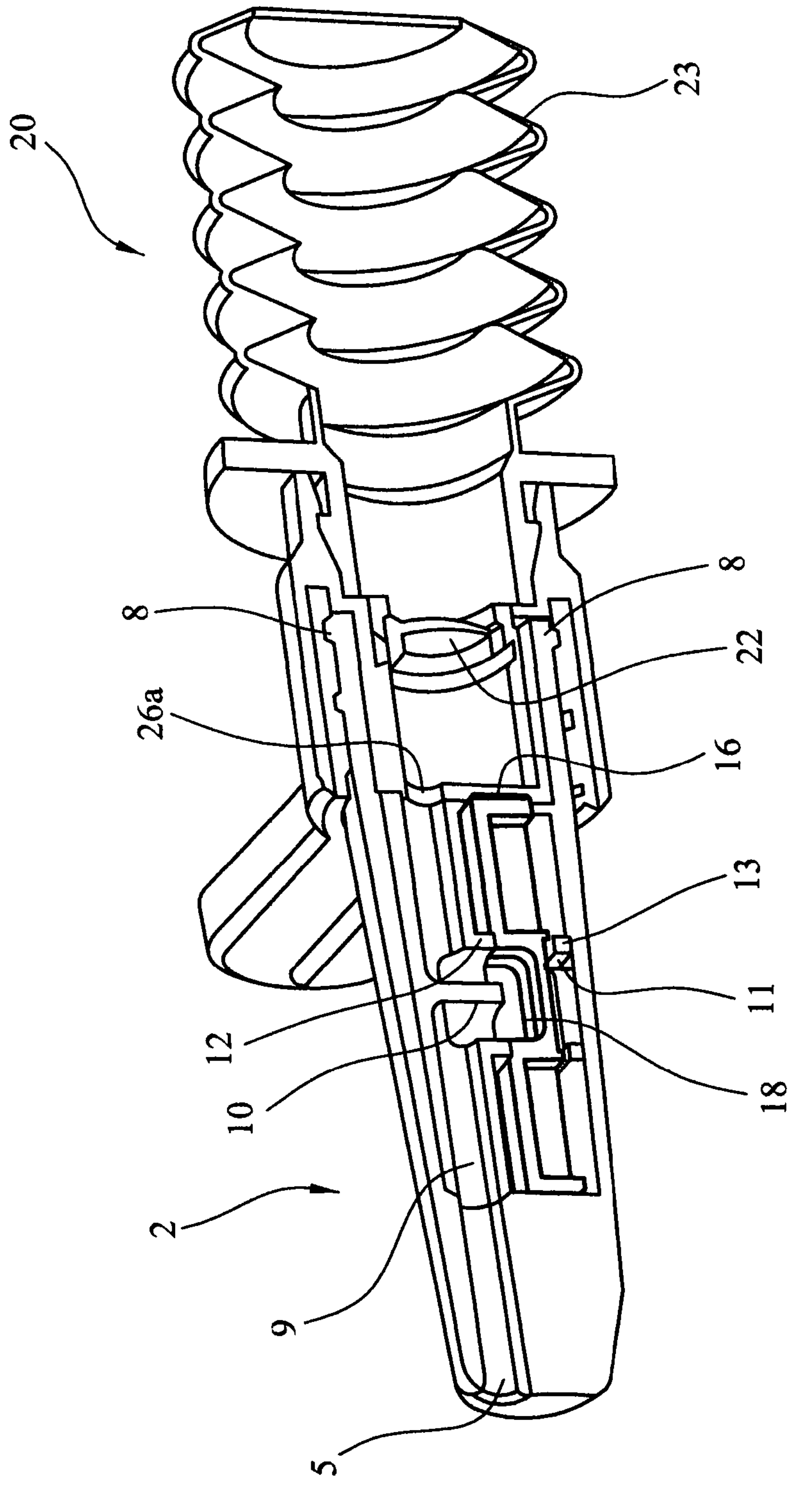
Figure 5:
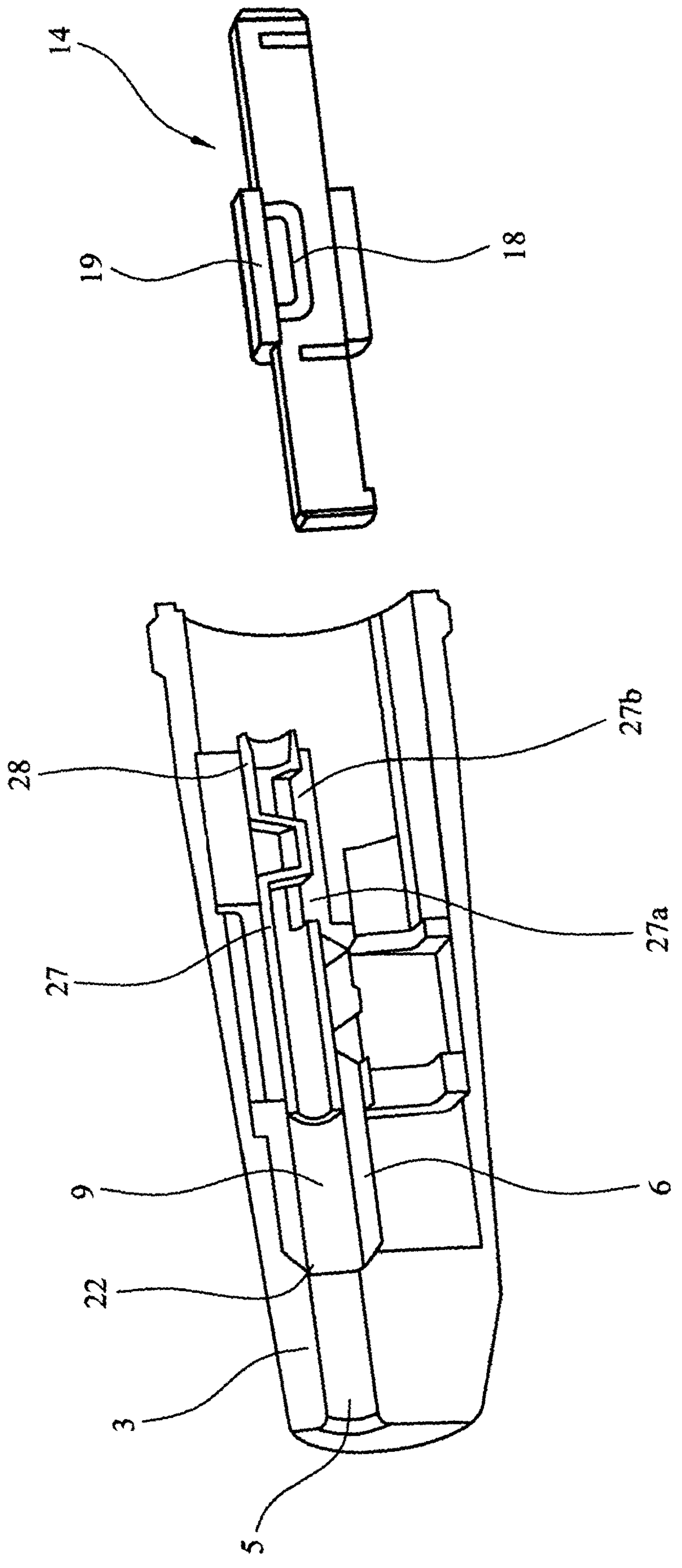
Figure 6:
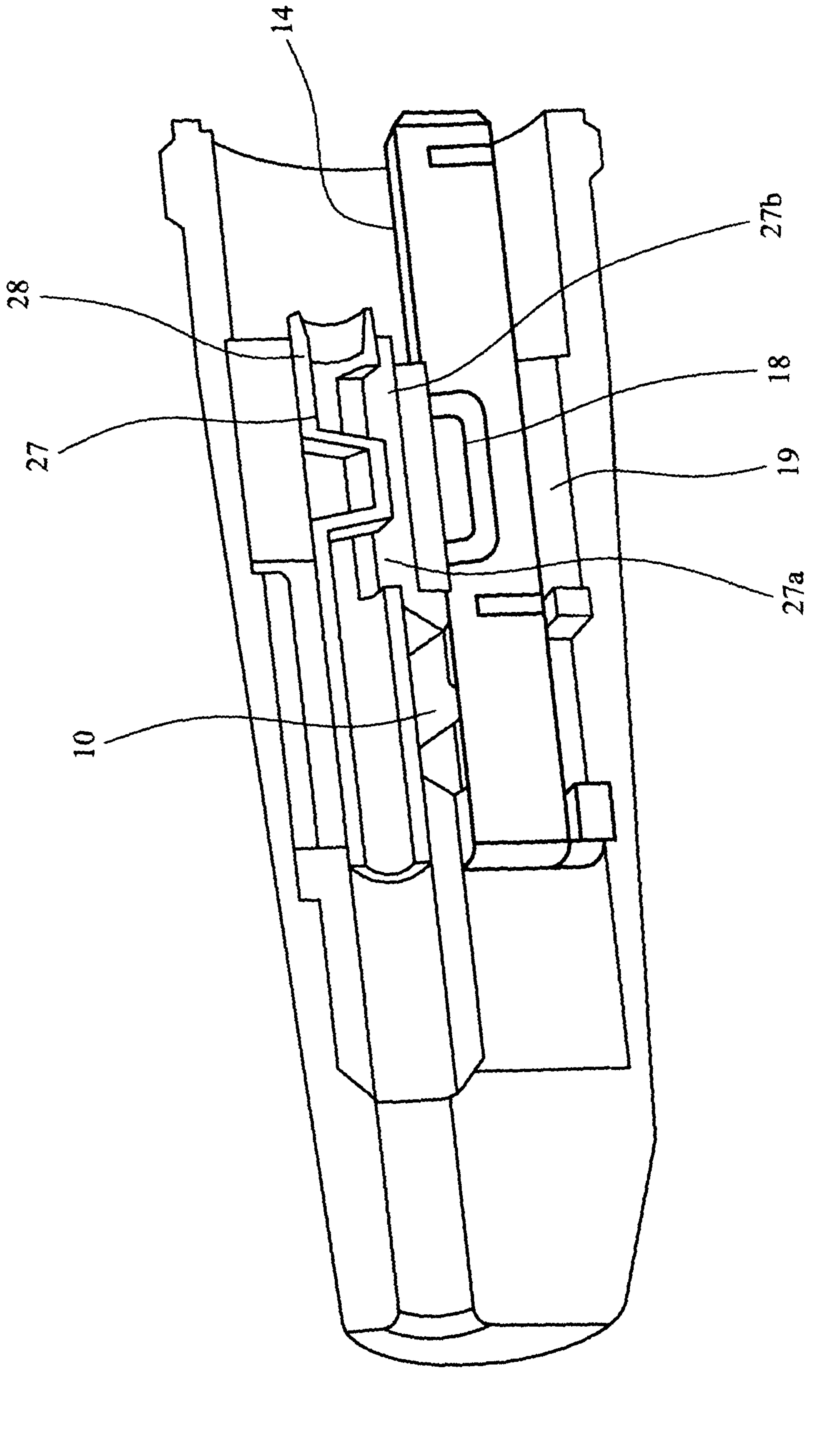
Figure 7:
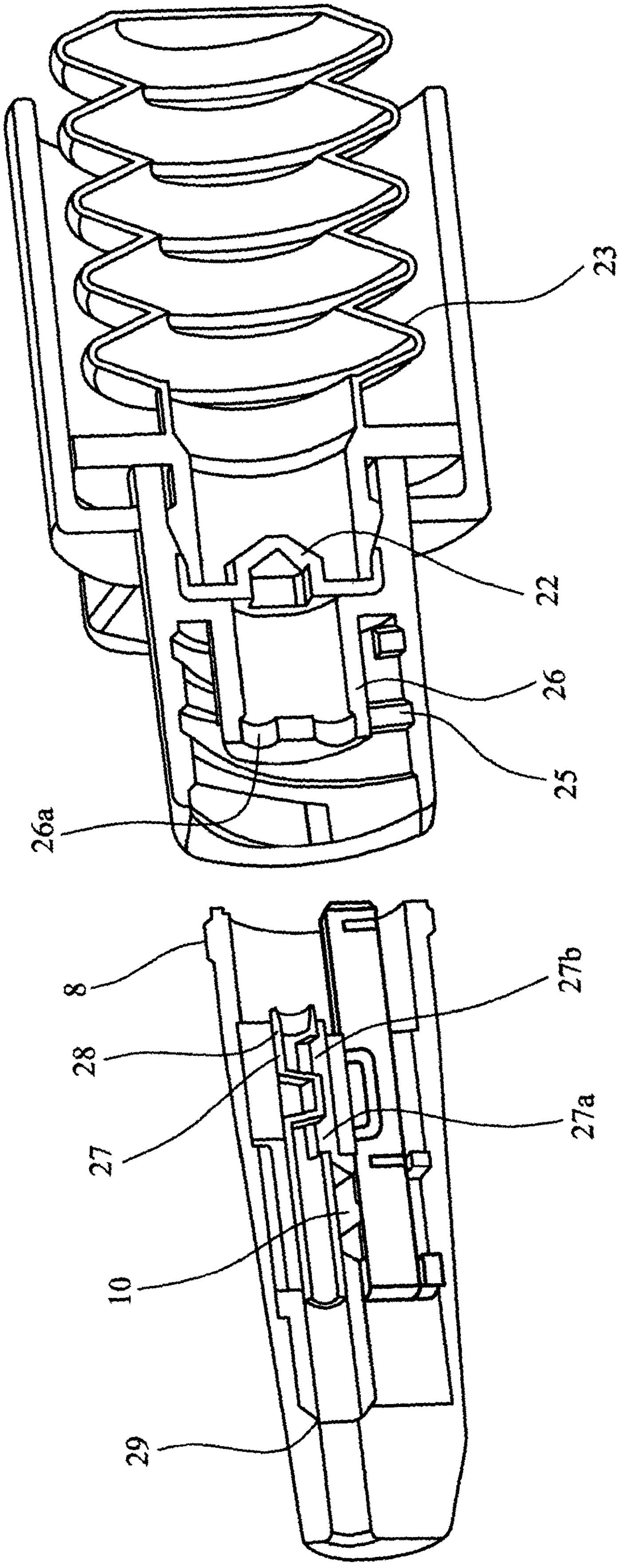
Figure 8A:
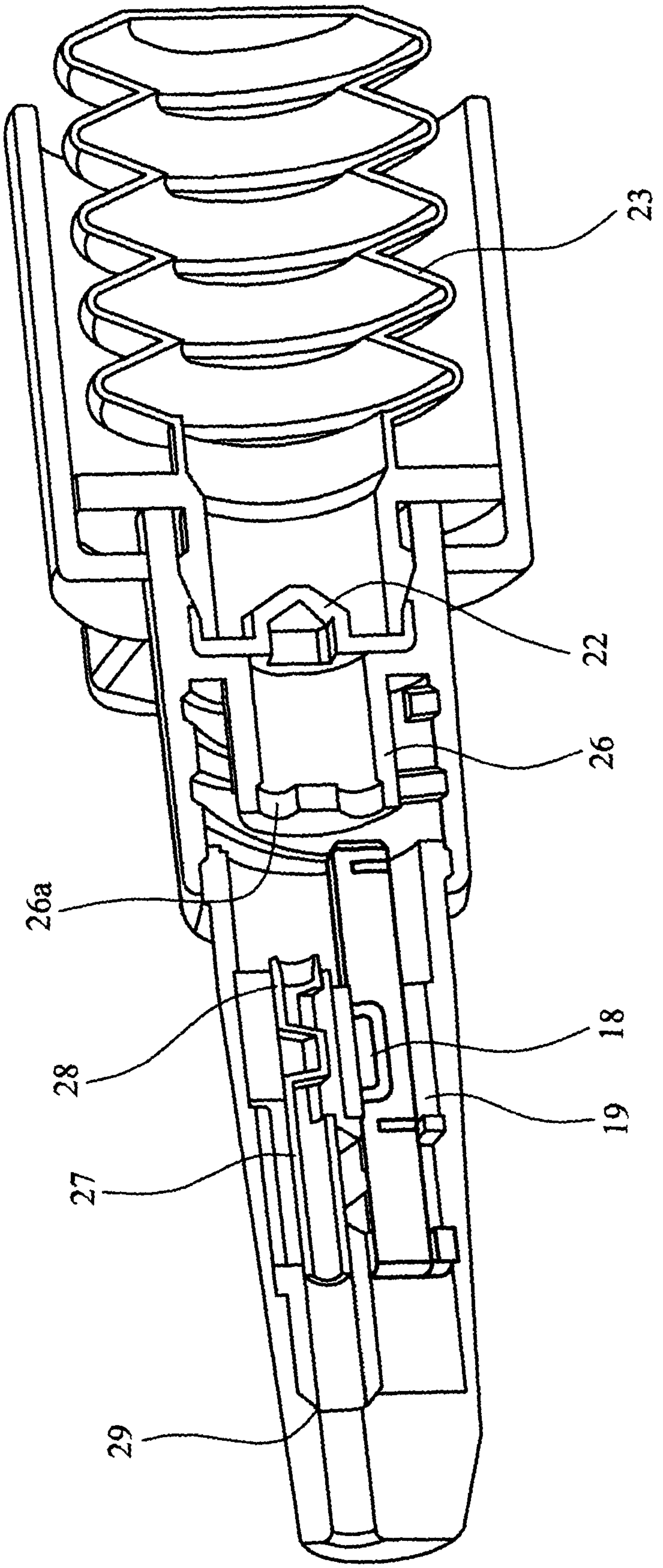
Figure 8B:
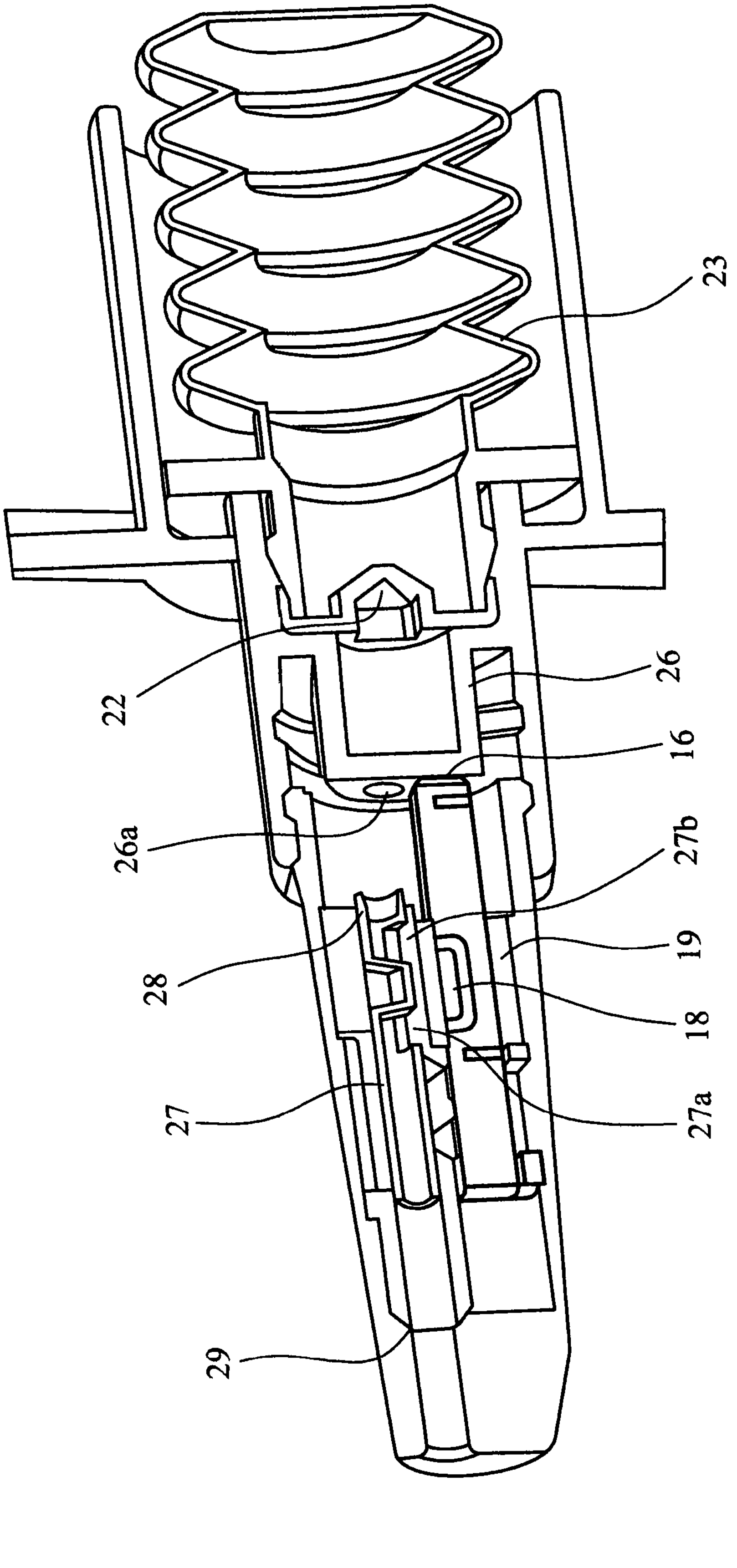
Figure 8C:
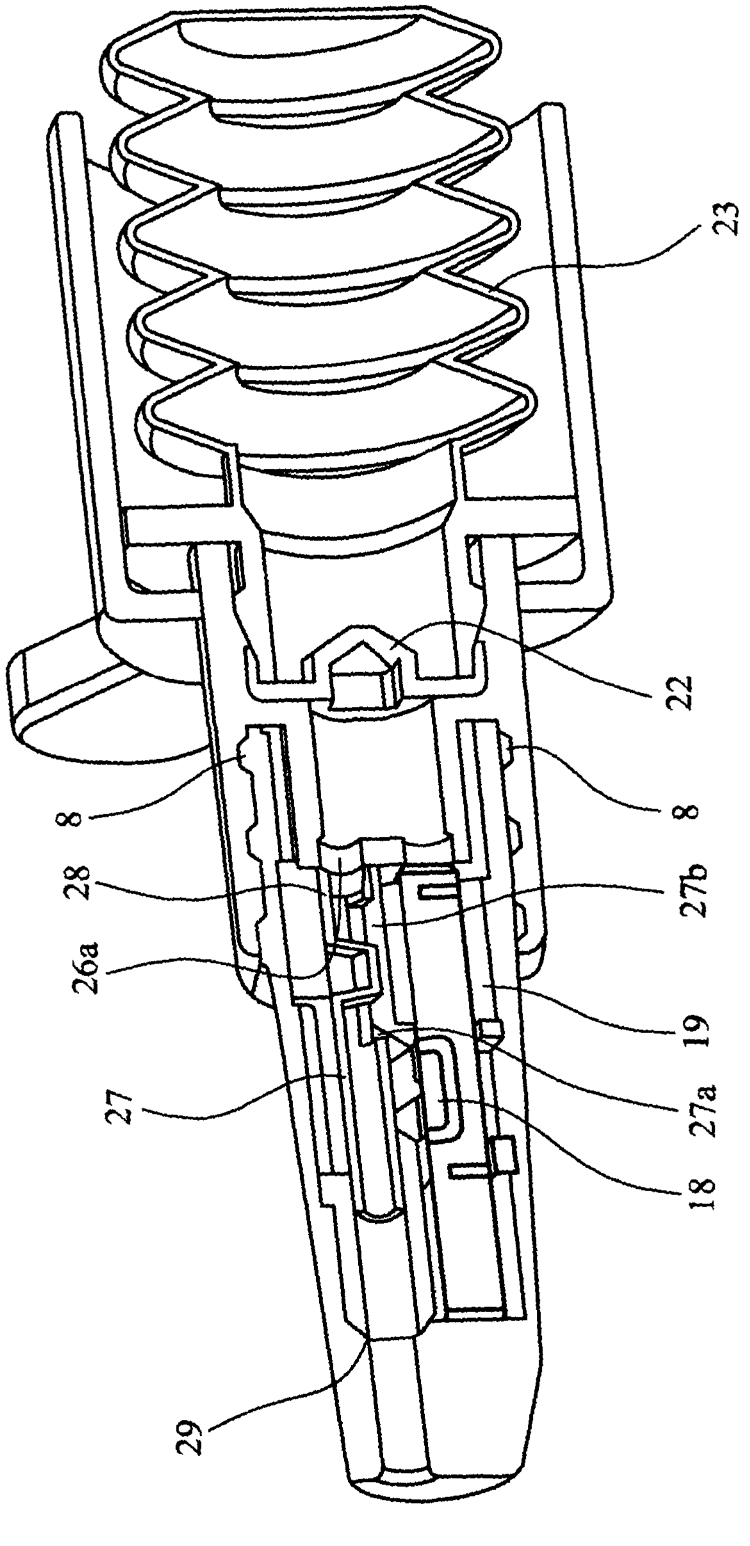
Figure 9:
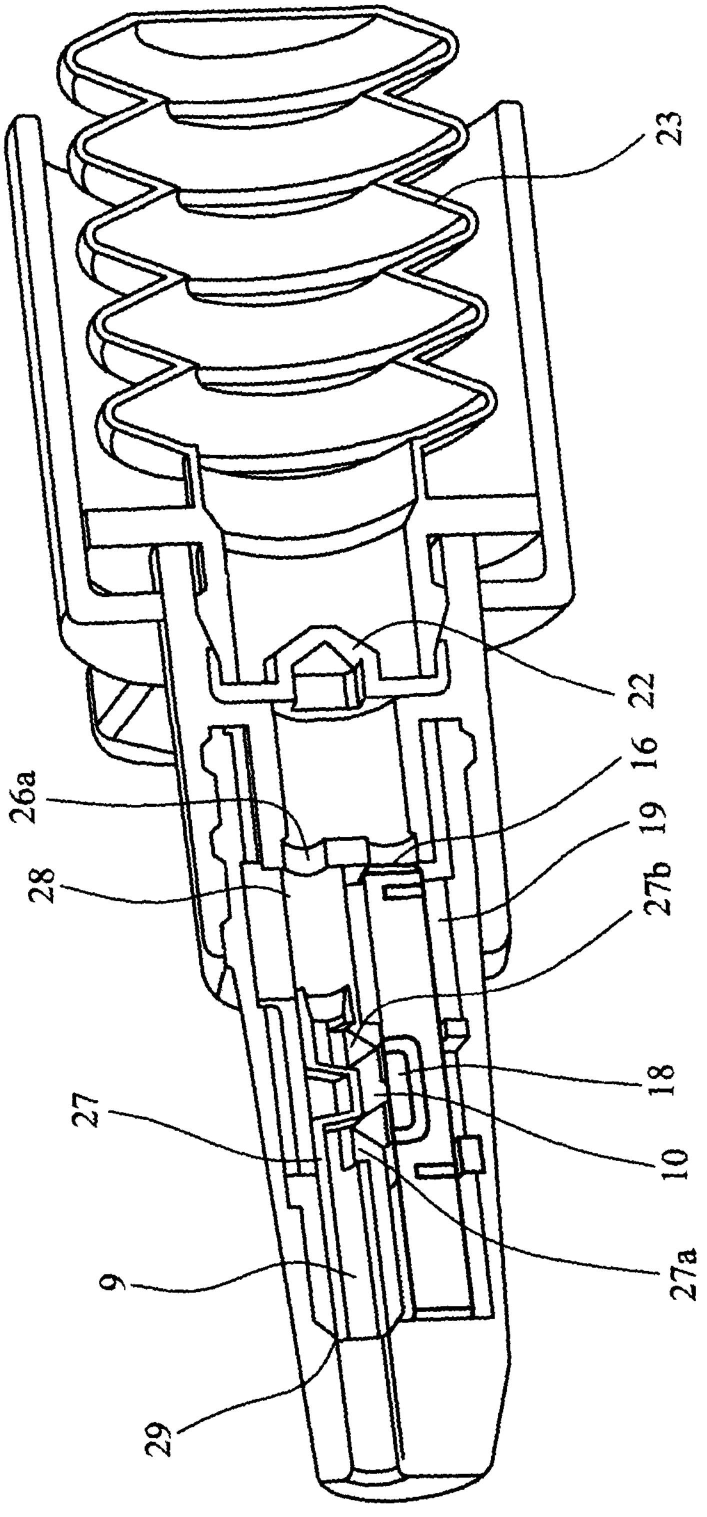
Figure 10:
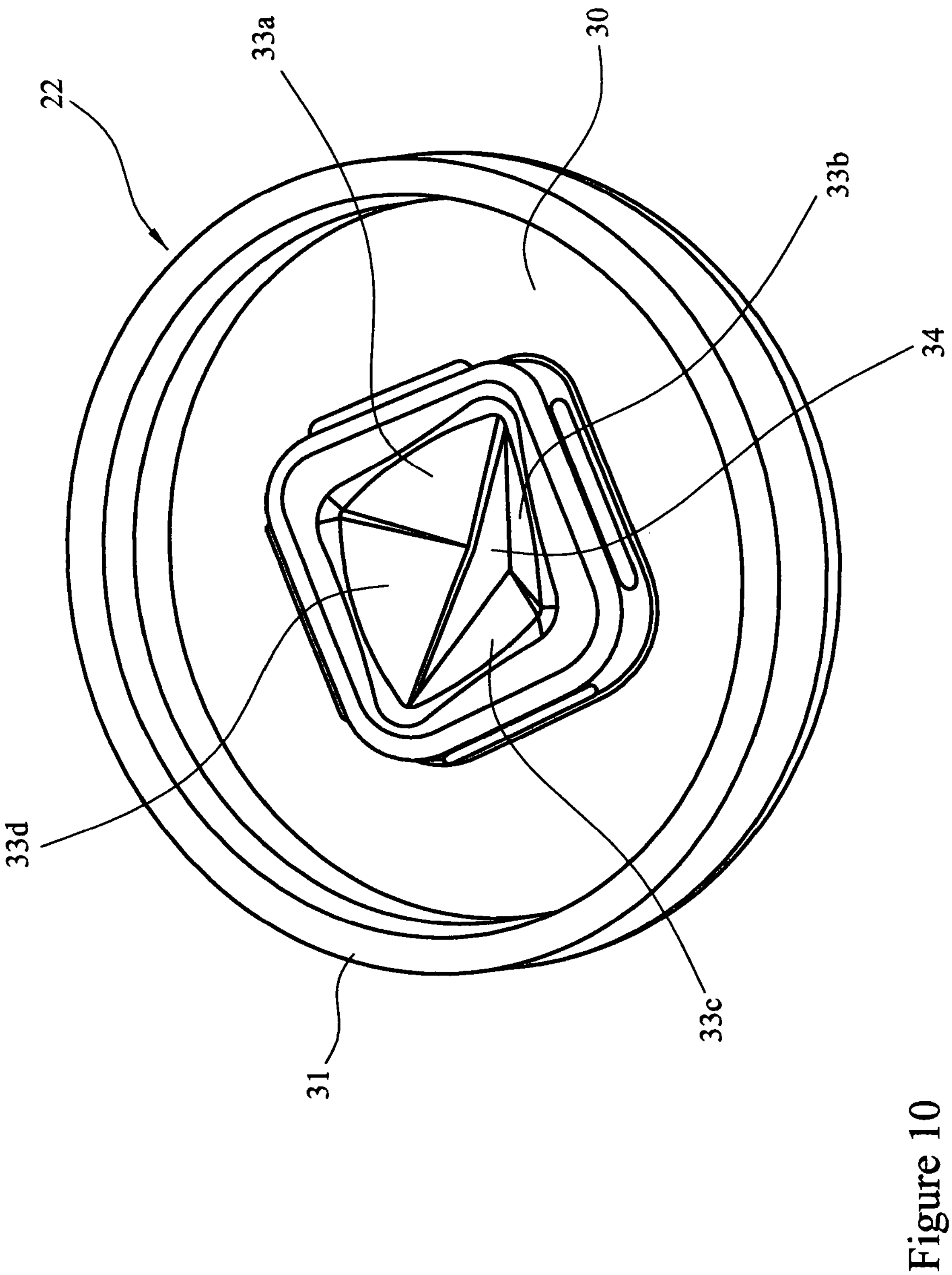
Figure 11:
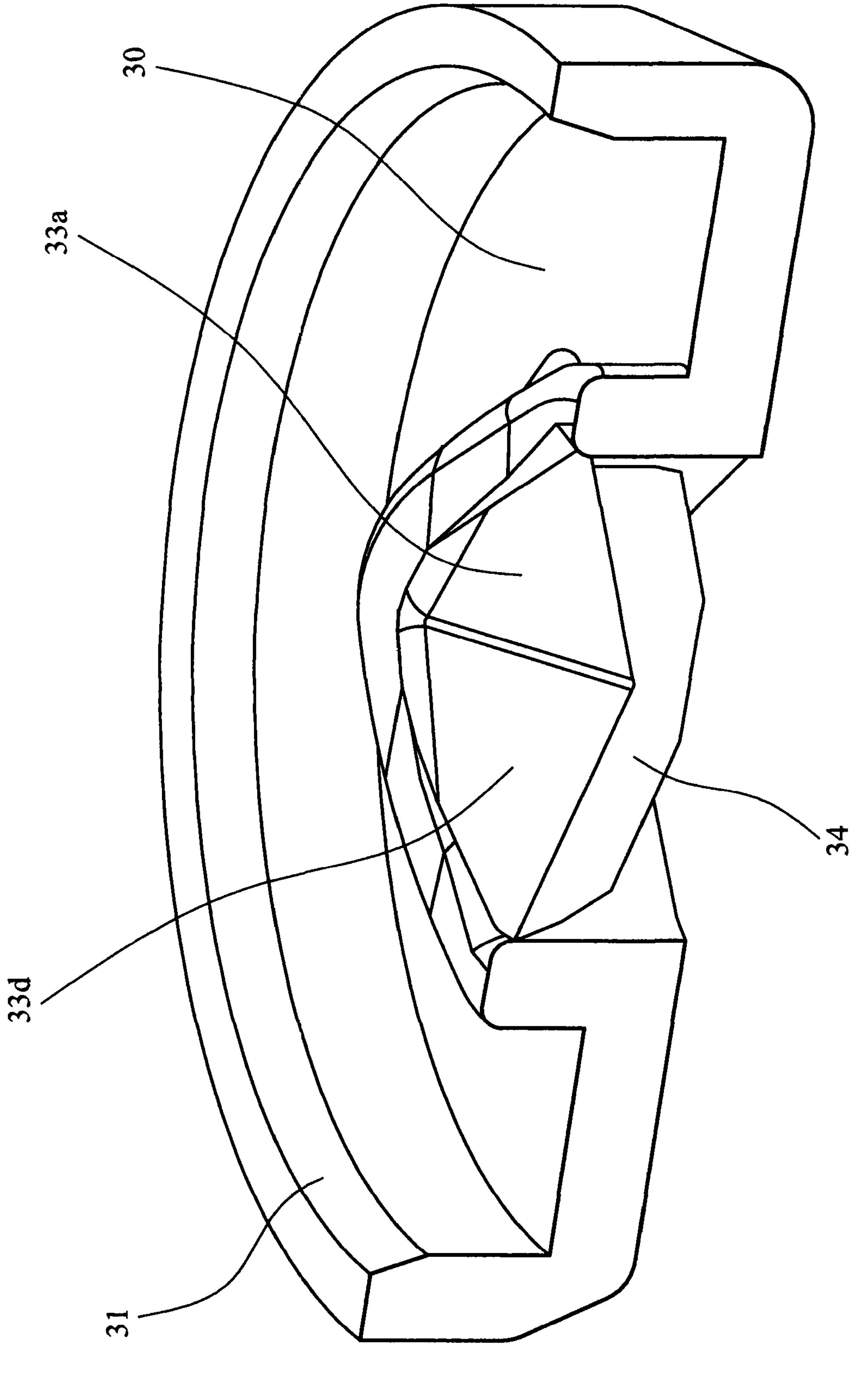
Figure 12:
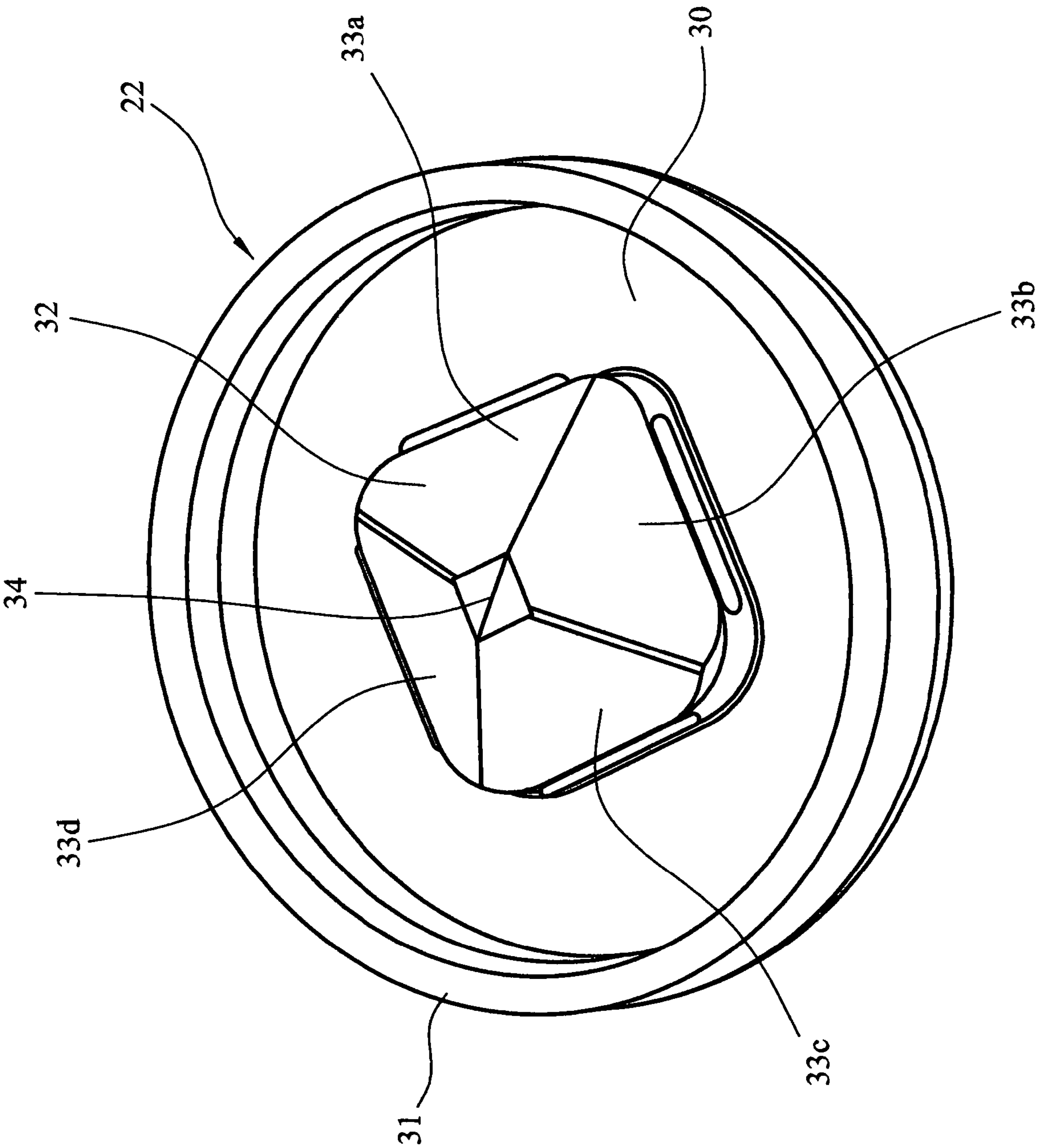

FIGS. 4*a*, 4*b* and 4*c* are cross-sectional views of a first element nozzle assembly attached to a second element and engaging with the cartridge assembly;

FIG. 5 is a cross-sectional view of a first element nozzle assembly including a shuttle valve and a cartridge assembly with a slidable outer sleeve;

FIG. 6 is a cross-sectional view of a first element nozzle assembly including a shuttle valve and a cartridge assembly with a slidable outer sleeve inserted into the nozzle;

FIG. 7 is a cross-sectional view of a first element nozzle assembly including a shuttle valve and a second element comprising an actuator provided with an air source and a valve;

FIGS. 8*a*, 8*b* and 8*c* are cross-sectional views of a first element nozzle assembly including a shuttle valve attached to a second element and engaging with the cartridge assembly;

FIG. 9 is a cross-sectional view of the complete assembly after activation;

FIG. 10 is a perspective view of a pyramid valve in the closed position;

FIG. 11 is a cross-sectional view of a pyramid valve in the closed position;

FIG. 12 is a perspective view of a pyramid valve in the open position; and

Figure 13:
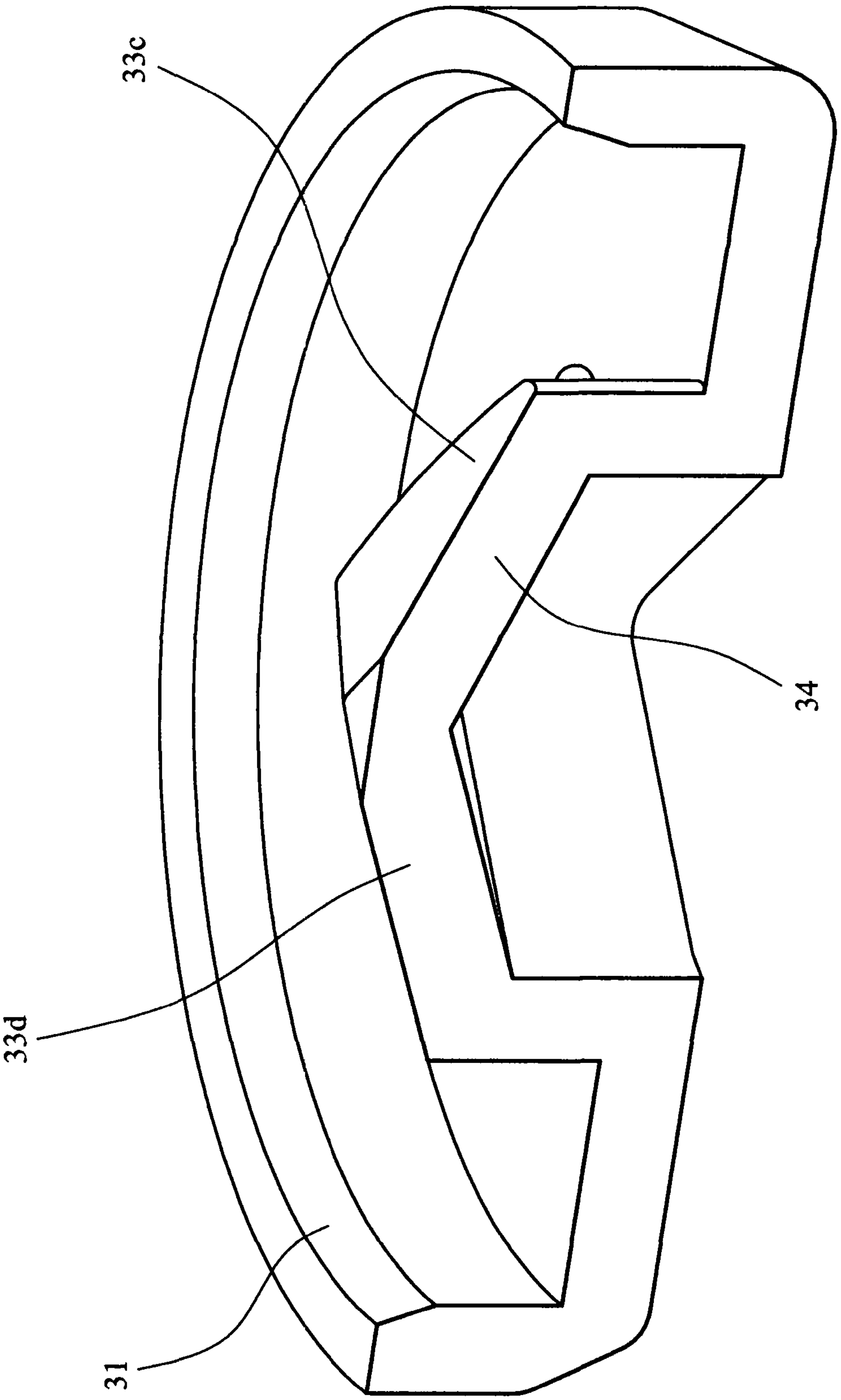

FIG. 13 is a cross-sectional view of a pyramid valve in the open position.

Figure 1:
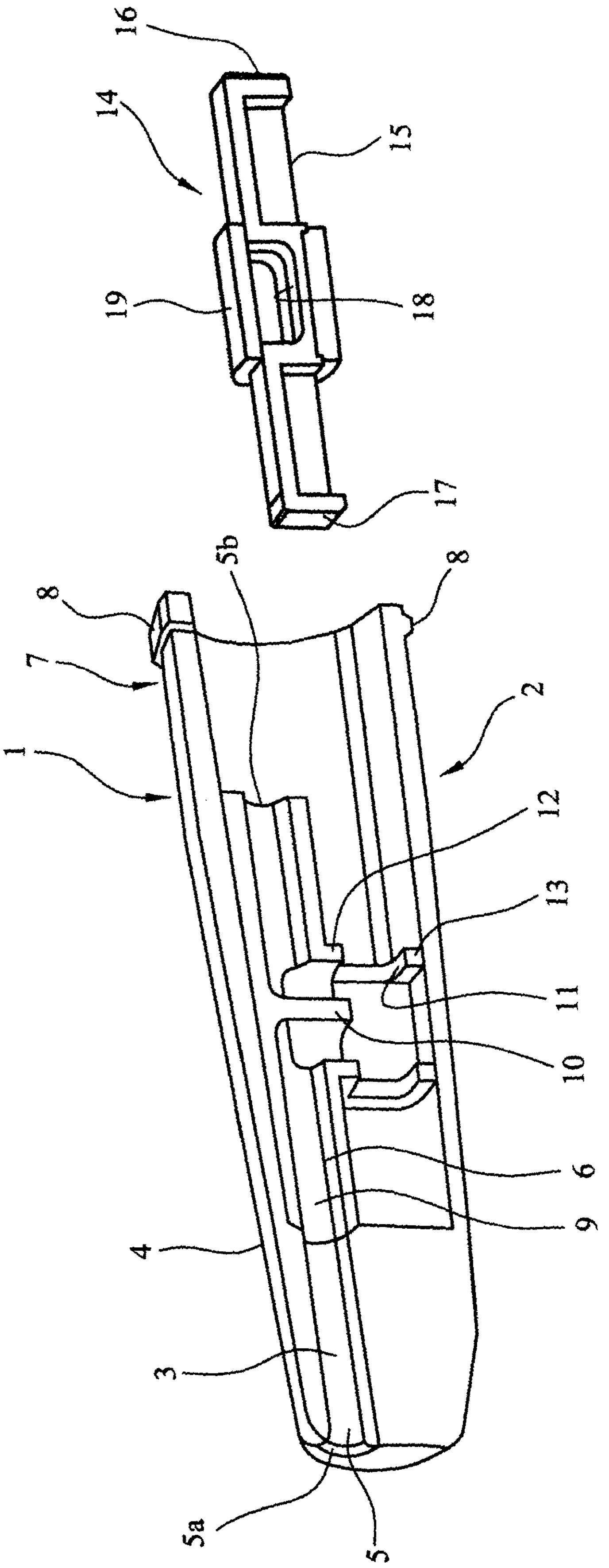

Referring to FIG. 1 a multi-unit dose dry powder medicament delivery device 1 comprises a first element 2. The first element 2 comprises a nozzle 3 located in a body 4, the nozzle 3 being provided with an airway 5 and an inner sleeve 6. At one end 7 the body 4 is provided with a circumferential rim 8. The airway 5 has an outlet 5*a* and an inlet 5*b*. The inner sleeve 6 is provided with an airway 9, which corresponds with the airway 5 of the nozzle. The airway 9 of the inner sleeve 6 is provided with a baffle 10 and a cartridge assembly seat 11 and cartridge facing lips 12 and 13.

A cartridge assembly 14 is also shown, said cartridge assembly comprising an elongate member 15 with a first end wall 16 and a second end wall 17. The elongate member 15 is provided with a cavity 18 for housing a medicament (not shown) and a closure sleeve 19.

Figure 2:
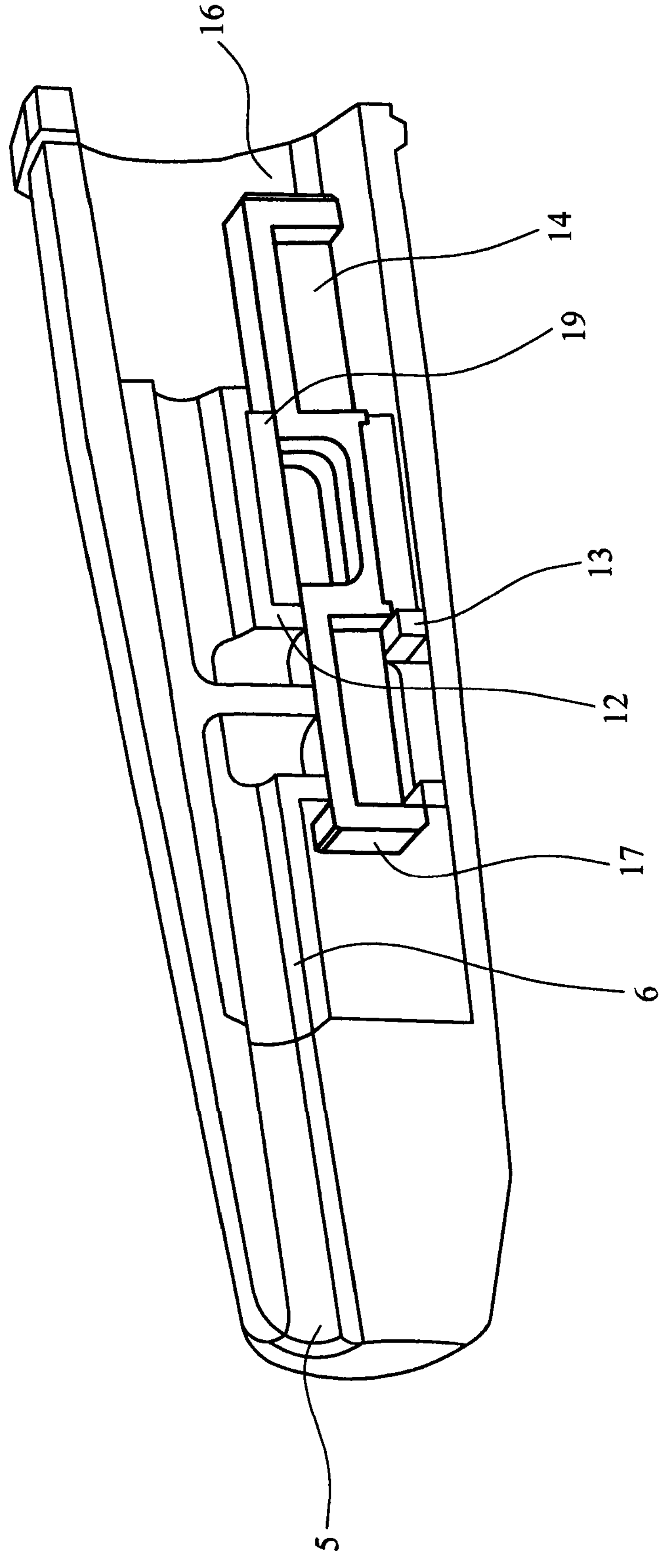
FIG. 2 is a cross-sectional view of a nozzle with an inner sleeve and a cartridge assembly inserted into the nozzle.

FIG. 2 illustrates the cartridge assembly 14 inserted into the body 4 such that the closure sleeve 19 abuts the cartridge facing lips 12 and 13.

Figure 3:
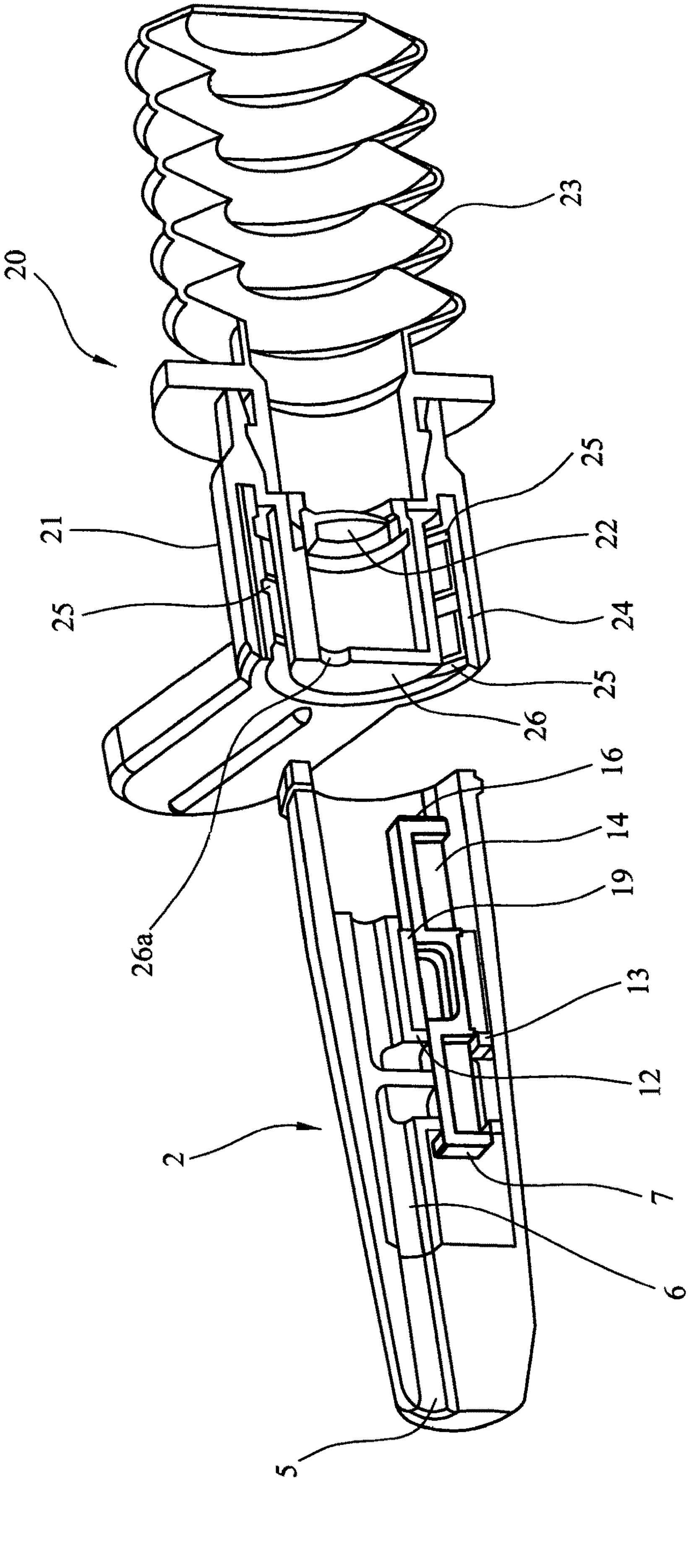
FIG. 3 is a cross-sectional view of a first element nozzle assembly and a second element comprising an actuator provided with an air source and a valve.

Referring to FIG. 3, the first element 2 is shown as described in FIGS. 1 and 2. Also shown is a second element 20 comprising an adaptor element 21, a burst valve 22 and bellows 23. The adaptor element 21 comprises a cylinder 24 with an internal screw thread 25 in the form of the helical grooves and a spigot 26 provided with an aperture 26*a*.

Referring to FIGS. 4*a*, 4*b* and 4*c*, in operation the second element 20 is attached to the first element 2, by locating the spigot 26 in the body 4 of the first element. The circumferential rim 8 of the first element 2 is located into the screw thread 25 of the second element 20.

When a user is ready to administer medication, the device is "primed". The body 4 of the first element 2 is held still and the second element 20 is rotated, screwing the adaptor element 21 onto the body 4 as the circumferential rim 8 is rotated in the helical grooves of the screw thread 25. As this is done, the spigot 26 engages with the first end wall 16 of the cartridge assembly 14 and pushes the cartridge assembly 14 within the body 4. As the adaptor element 21 is screwed further onto the body 4 the spigot 26 continues to engage with the first end wall 16 of the cartridge assembly 14. The closure sleeve 19 of the cartridge assembly engages with the cartridge facing lips 12 and 13 of the inner sleeve 6, causing the travel of closure sleeve 19 to stop whilst the (now open) cavity 18 continues to travel to the cartridge assembly seat 11, located under and aligned with the airway 9.

To administer the medicament (dry powder formulation) the bellows 23 is depressed to cause air pressure to build in bellows 23 to a point where the burst valve 22 opens releasing a burst of air into airway 9. The burst of air travels through the apertured spigot 26, down the airway 9 until it hits baffle 10 which deflects the air into the open cavity 18, thus entraining the dry powder formulation contained in the cavity 18 into the air stream and out via the airway 5 of the nozzle 3.

After administration, the first element 2 is unscrewed from the second element 20 and can be discarded. The second element 20, comprising an adaptor element 21 a burst valve 22 and bellows 23, can be retained for use in conjunction with a first element 2 and any subsequent elements.

FIGS. 5, 6, 7, 8*a*, 8*b*, 8*c* and 9 illustrate a further embodiment of the multi-unit dose medicament delivery device. In this embodiment the airway 9 of the of the inner sleeve 6 is provided with a shuttle valve 27. The shuttle valve 27 is held in the closed position by a detent 28 in the inner sleeve 6. The shuttle valve 27 is dimensioned such that in the closed position it blocks both airway 9 and airway 5. In addition, the nozzle 3 is provided with a stop 29 capable of arresting movement of the shuttle valve 27. The shuttle valve 27 is provided with orifices 27*a* and 27*b*.

The use of a shuttle valve is advantageous in that it acts to prevent powder spillage, for example if the device is inverted and/or shaken after being "primed" but before the medicament is administered.

The operation of the multi-unit dose medicament delivery device of this embodiment is the same as herein described for FIGS. 1 to 4.

As the spigot 26 abuts the shuttle valve 27 it engages with it and pushes the shuttle valve 27 to release it from detent 28. At this point the airways 5 and 9 remain closed preventing any powdered medicament (not shown) from escaping from the device.

The procedure to administer the drug is as described above for the first embodiment. When air is released through the burst valve 22 the compressed air enters the shuttle valve 27 driving the shuttle valve 27 forwards to the stop 29. The orifices 27*a* and 27*b* of the shuttle valve 27 align with the airway 9, such that the air blast can then pass through the shuttle valve 27, airway 9, the medicament cavity 18, entraining the powdered medicament in the airflow, and through airway 5.

Referring to FIGS. 10 to 13 the burst valve 22 comprises a moulded flexible polymer disc 30 provided with a circumferential flange 31 to provide a sealing ring. Substantially in the centre of the disc there is provided a four sided pyramid structure 32 which forms a closure. The four sided pyramid structure 32 is provided with walls 33*a*, 33*b*, 33*c* and 33*d*. The pyramid structure 32 is provided with a slit 34 cut along a diagonal of the pyramid 32. In the valve's dormant state the slit 34 remains closed.

In the operation of the assembled device herein described (i.e. depressing the bellows 23), air pressure acts upon the outer surface of the pyramid 32 and walls (33*a*, 33*b*, 33*c* and 33*d*). The pyramid and wall structure is inherently a strong structure and the material (TPE) is compressed with the slit 34 being forced tightly dosed, however as pressure builds the pyramid is overcome and collapses and the slit 34 opens to create an orifice 35, allowing the compressed air to pass through the orifice 35. When the air pressure has diminished to ambient pressure, the pyramid 32 regains its moulded form. As the bellows 23 is released the outer surface of the pyramid 32 and walls (33*a*, 33*b*, 33*c* and 33*d*) are subjected to a negative pressure whilst the inner surfaces are subject to ambient pressure, the result is that the walls (33*a*, 33*b*, 33*c* and 33*d*) deflect outwardly relieving the forces on the slit 34, the effect being that air can 'leak' back into the bellows.

The invention claimed is:

1. A multi-unit dose dry powder medicament delivery device comprising:

- a first element comprising a single use nozzle located in a body which is at least partially lined with an inner sleeve, said inner sleeve comprising an airway and a cartridge seat; and
- a second element adapted to be releasably attached to the first element, said second element comprising an actuator provided with an air source and a valve;
- wherein the inner sleeve is provided with a shuttle valve which is dimensioned such that in the closed position it blocks the airway only until the device is primed by a user; wherein the shuttle valve is provided with two orifices and the nozzle is provided with a stop capable of arresting movement of the shuttle valve; and
- wherein the actuator in the second element comprises a spigot element which, when inserted into the first element, pushes the medicament container into position for delivery of the medicament.

2. A multi-unit dose dry powder medicament delivery device according to claim 1 wherein the inner sleeve comprises at least one baffle element.

3. A multi-unit dose dry powder medicament delivery device according to claim 1 wherein the releasable attachment of the first element to the second element comprises a screw fit.

4. A multi-unit dose dry powder medicament delivery device according to claim 1 wherein the shuttle valve is provided with a pair of orifices which, when a device is primed, align with the airway of the device.

5. A multi-unit dose dry powder medicament delivery device according to claim 1 comprising a medicament cartridge comprising an elongate member provided with an inset cavity which acts as a medicament reservoir.

6. A multi-unit dose dry powder medicament delivery device according to claim 1 comprising a medicament cartridge provided with a closure sleeve.

7. A multi-unit dose dry powder medicament delivery device according to claim 6 wherein the closure sleeve is slidably mounted around the inset cavity.

8. A multi-unit dose dry powder medicament delivery device according to claim 1 wherein the spigot element is provided with at least one aperture to enable air to pass from the air source and valve through the spigot.

9. A multi-unit dose dry powder medicament delivery device according to claim 1 wherein the valve is a burst valve.

10. A multi-unit dose dry powder medicament delivery device according to claim 1 wherein the device is suitable for the treatment of a respiratory disorder.

11. A multi-unit dose dry powder medicament delivery device according to claim 10 wherein the device is a nasal inhaler.

12. A method of delivering a medicament to a patient which comprises the use of a dry powder medicament delivery device according to claim 1;

said method comprising the steps of:

(i) engaging the nozzle;

(ii) screwing in the nozzle and priming the device; and (iii) actuating the device.

13. A multi-unit dose dry powder medicament delivery device kit comprising:

a first element comprising a single use nozzle, said nozzle being located on a body which is at least partially lined with an inner sleeve, said inner sleeve comprising an airway and a cartridge seat;

a second element adapted to be releasably attached to the first element, said second element comprising an actuator provided with an air source and a valve;

wherein the inner sleeve is provided with a shuttle valve which is dimensional such that in the closed position it blocks the airway only until the device is primed by a user; wherein the shuttle valve is provided with two orifices and the nozzle is provided with a stop capable of arresting movement of the shuttle valve; and wherein the actuator in the second element comprises a spigot element which, when inserted into the first element, pushes the medicament container into position for delivery of the medicament; and at least one cartridge comprising a dry powder medicament.

* * * * *